(12) United States Patent
Sanguinetti et al.

(10) Patent No.: US 9,668,953 B2
(45) Date of Patent: Jun. 6, 2017

(54) ANTI-AGING ANTIOXIDANT NUTRITIONAL SUPPLEMENT FOR THE IMPROVEMENT OF THE INTEGUMENTARY SYSTEM

(71) Applicant: MINERVA Research Labs Ltd, London (GB)

(72) Inventors: Catone Tony Sanguinetti, London (GB); Thein Aung, London (GB); Sara Sibilla, London (GB); Vidhi Patel, London (GB)

(73) Assignee: MINERVA Research Labs Ltd, London (GB)

( * ) Notice: Subject to any disclaimer, the term of this patent is extended or adjusted under 35 U.S.C. 154(b) by 0 days.

(21) Appl. No.: 14/812,262

(22) Filed: Jul. 29, 2015

(65) Prior Publication Data
US 2016/0030311 A1    Feb. 4, 2016

(30) Foreign Application Priority Data

Jul. 30, 2014 (IT) .............................. TO2014A0608

(51) Int. Cl.
| | |
|---|---|
| *A61K 8/35* | (2006.01) |
| *A23L 33/28* | (2016.01) |
| *A23L 5/00* | (2016.01) |
| *A23L 33/105* | (2016.01) |
| *A23L 33/18* | (2016.01) |
| *A61K 8/66* | (2006.01) |
| *A61K 8/34* | (2006.01) |
| *A61K 8/49* | (2006.01) |
| *A61Q 19/08* | (2006.01) |
| *A61K 8/67* | (2006.01) |
| *A61K 8/31* | (2006.01) |
| *A61K 8/97* | (2017.01) |
| *A61K 8/65* | (2006.01) |
| *A61K 8/73* | (2006.01) |

(52) U.S. Cl.
CPC ................ *A61K 8/355* (2013.01); *A23L 5/00* (2016.08); *A23L 33/105* (2016.08); *A23L 33/18* (2016.08); *A23L 33/28* (2016.08); *A61K 8/31* (2013.01); *A61K 8/347* (2013.01); *A61K 8/4946* (2013.01); *A61K 8/65* (2013.01); *A61K 8/66* (2013.01); *A61K 8/67* (2013.01); *A61K 8/671* (2013.01); *A61K 8/673* (2013.01); *A61K 8/676* (2013.01); *A61K 8/735* (2013.01); *A61K 8/97* (2013.01); *A61Q 19/08* (2013.01); *A23V 2002/00* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 2006/0222699 A1* | 10/2006 | Gilinski | ............... A61K 9/4816 424/451 |
| 2006/0251608 A1 | 11/2006 | Wachsberg et al. | |
| 2010/0055138 A1* | 3/2010 | Margulies | ................ A61K 8/02 424/401 |

FOREIGN PATENT DOCUMENTS

| | | |
|---|---|---|
| EP | 2 532 252 | 12/2012 |
| WO | WO 2008/079898 | 7/2008 |

OTHER PUBLICATIONS

Zhuang et al. Optimization of antioxidant activity by response surface methodology in hydrolysates of jellyfish (*Rhopilema esculentum*) umbrella collagen. J Zhejiang Univ Sci B (2009), v10(8), p. 572-579.*

Italian Search Report and Written Opinion for IT TO2014A000608 dated Mar. 19, 2015, seven pages.

* cited by examiner

*Primary Examiner* — Scott Long
*Assistant Examiner* — Sean C Barron
(74) *Attorney, Agent, or Firm* — Nixon & Vanderhye P.C.

(57) ABSTRACT

A liquid anti-aging antioxidant nutritional supplement comprising collagen, carnosine, CoEnzyme Q10 and Resveratrol particularly suitable for reducing oxidative damage to the integumentary system.

3 Claims, 2 Drawing Sheets

ANTI-AGING ANTIOXIDANT NUTRITIONAL SUPPLEMENT FOR THE IMPROVEMENT OF THE INTEGUMENTARY SYSTEM

This application claims priority to IT Patent Application No. TO2014A000608 filed Jul. 30, 2014, the entire content of which is hereby incorporated by reference.

FIELD OF THE INVENTION

This disclosure concerns a nutritional supplement particularly suitable to counteract the oxidative damage in the integumentary system.

BACKGROUND OF THE INVENTION

Oxidative stress is defined as a disturbance in the balance between the production of reactive oxygen species (ROS) and antioxidant defenses (Finkel and Holbrook 2000), (Kunwar et al, 2011).

ROS are molecules containing oxygen reactive molecules; examples of ROS include free radicals, oxygen ions and peroxides.

ROS are formed as a natural byproduct of the normal metabolism of oxygen and have important roles in cell signaling and homeostasis.

ROS may also act by driving several molecular pathways that play important roles in different pathologic conditions such as cancer, heart diseases and diabetes.

The over-production of peroxides and free radicals leads to damage in the components of the cell, including proteins, lipids and DNA. Moreover, some ROS may act as cellular messengers in reduction/oxidation (redox) signaling between cells. Therefore, oxidative stress can cause disruptions in normal mechanisms of cell signaling.

Thus, the use of oxygen by cells of aerobic organisms generates potentially deleterious reactive oxygen metabolites.

The amount of oxidative damage can increase with the age of an organism and it can be a major factor able to cause senescence (Sohal and Weindruch 1996).

The main point emerging from research studies is that molecular oxidative damage during aging is ubiquitous, significant and increases exponentially with age.

The main causes of an age-associated increase in the amount of oxidative stress can be linked to an increase in the rate of generation of reactive oxygen metabolites (ROMs), a decline in anti-oxidative defenses, a decline in the efficiency of repair or removal of damaged molecules.

Hydrogen peroxide production by mitochondria is also one of the main sources of oxidative stress and in mammals increases with age in several different organs (Turrens and McCord 1990).

A recent study has investigated the effect of gender, age and treatment time on brain oxidative stress and spatial memory deficits induced by d-galactose (d-gal) in mice. Female mice did not show spatial memory impairment, even in the presence of increased amounts of brain reactive oxygen species (ROS). In contrast, male mice receiving the same amount of d-gal showed spatial memory deficits and significant increase in oxidative stress markers (Hao et al, 2014).

Interestingly, another recent study published in 2014, recruited a total of 478 workers (272 men and 206 women) from a coke oven plant. The study found that women were more susceptible than men to oxidative stress and chromosome damage induced by polycyclic aromatic hydrocarbons (PAHs), which adds potential evidence underlying gender differences in PAH exposure-related lung carcinogenesis (Guo et al, 2014).

The skin, together with hair and nails, is the main organ of the integumentary system, and represents the first and main barrier to the external environment.

In the skin, free radical damage can cause deterioration of the supportive connective tissue, resulting in decreased elasticity and resilience. Oxidative stress, moreover, may impair hair follicle function, causing androgenetic alopecia (pattern baldness) in men and women.

Skin exposure to solar ultraviolet radiation initiates photochemical reactions which lead to ROS formation and when their production gets out of control, oxidative stress occurs. When this happens, ROS (together with enzymes released from granules within the white blood cells) injure or even kill cells, damage DNA and attack enzymes and other compounds.

The skin possesses defense mechanisms which interact with toxicants and counteract their deleterious effect (such as non-enzymatic and enzymatic molecules that function as potent antioxidants).

These defenses, although highly effective, have limited capacity and can be overwhelmed leading to increased ROS levels and to the development of dermatological diseases.

It is generally agreed that there is a correlation between ageing and the accumulation of oxidatively damaged proteins, lipids, and nucleic acids (Levine and Stadtman 2001).

A recent study has shown that exposure of skin to a number of chemical and physical environmental agents induces oxidative stress that leads to the induction of cutaneous lipid peroxidation with concomitant modulation in the levels of antioxidant and drug-metabolizing enzymes.

One approach to prevent or treat these ROS-mediated disorders is based on the administration of different antioxidants wherein the term antioxidant refers to any molecule capable of stabilizing or deactivating free radicals before they cause damage in healthy cells.

SUMMARY OF THE INVENTION

The purpose of the present description is to provide a nutritional supplement with a high antioxidant capability that is able to slow the natural aging process by counteracting the formation of free radicals in the body through the synergistic effects exerted by the active ingredients.

According to the invention, the above object is achieved thanks to the subject matter recalled specifically in the ensuing claims, which are understood as forming an integral part of this disclosure.

An embodiment of the present description provides a nutritional supplement comprising collagen, carnosine, CoEnzyme Q10 and Resveratrol.

In another embodiment, the nutritional supplement further comprises an emulsion comprising borage seed oil and primrose oil.

In another embodiment, the nutritional supplement comprises at least one further ingredient selected among hyaluronic acid, black pepper extract, lycopene.

In a further embodiment the nutritional supplement herein described also includes at least one of acai berry, pomegranate, vitamins, preferably vitamin C and vitamin A.

In another embodiment the food supplement herein described also includes minerals, additives and flavouring substances.

BRIEF DESCRIPTION OF THE DRAWING

The invention will now be described, by way of example only, with reference to the enclosed figure of drawing, wherein.

DETAILED DESCRIPTION OF THE INVENTION

Figure 1:
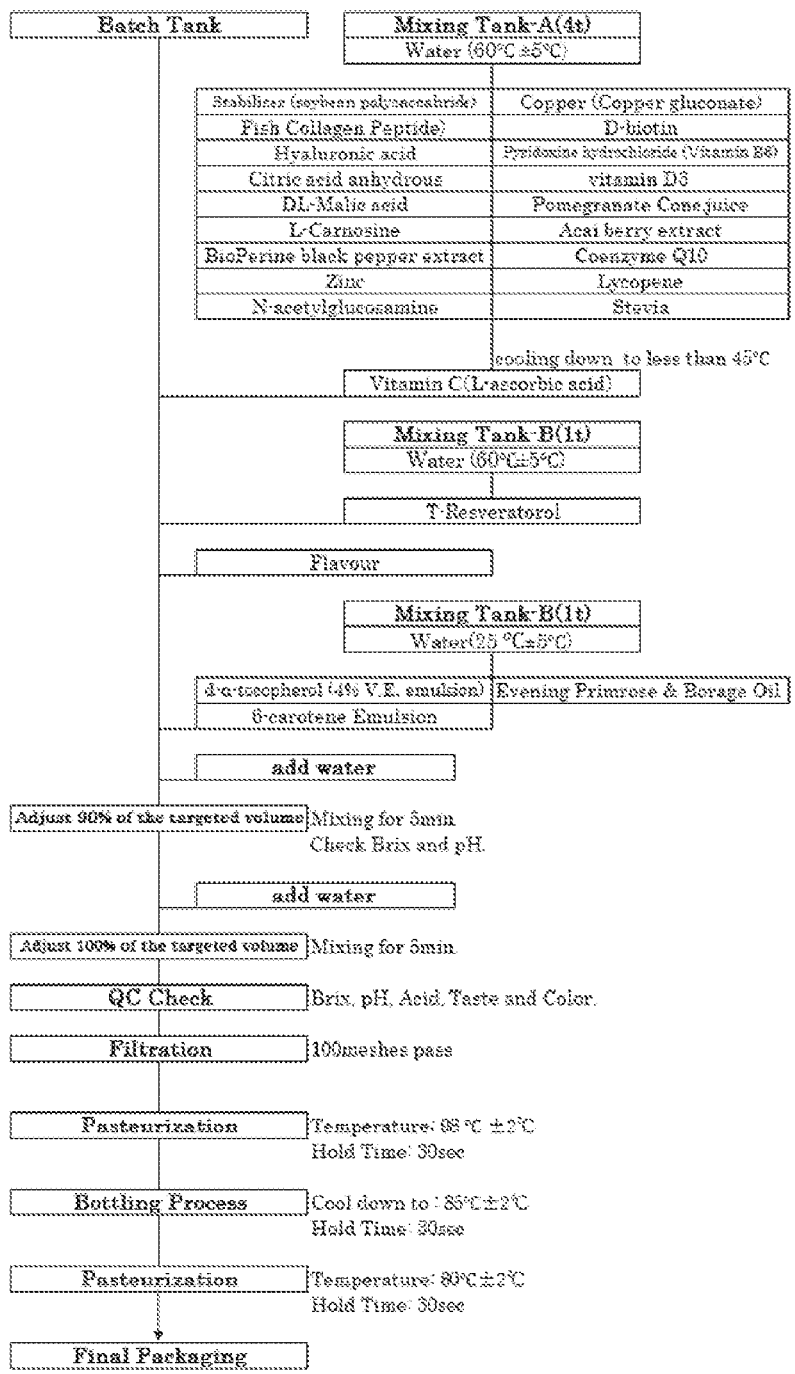
FIG. 1 shows a manufacturing process diagram of an embodiment of a nutritional supplement disclosed in the present description.
Figure 2:
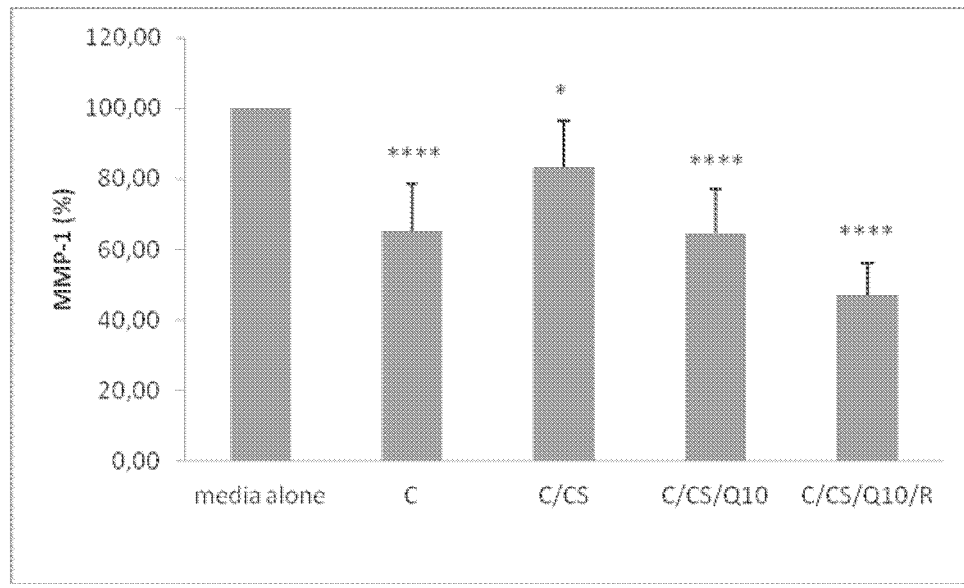
FIG. 2 shows the effect of nutritional supplement main ingredients on MMP-1 synthesis by normal human dermal fibroblasts (NHDF). MMP-1 was measured in supernatants of NHDF grown in 24 well plates and incubated in media (0) plus various combinations of nutritional supplement main ingredients (see tables 5 and 6 for description of additions) for 48 hours. Data was expressed as % of media control, normalised to 100% in each experiment and is presented as mean±SEM of 3 independent experiments.*indicates $P<0.05$,**** $P<0.0001$. Media is $5.6\pm1.7$ ng/ml.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

An embodiment of the present disclosure provides a nutritional supplement comprising collagen, carnosine (preferably L-carnosine), CoEnzyme Q10 and Resveratrol (preferably T-resveratrol).

The nutritional supplement herein described is endowed with a high antioxidant capability and it is able to reduce the oxidative damage and improve the integumentary system.

In particular, it exerts an improvement in the skin condition by increasing hydration and elasticity, by decreasing depth and total surface of wrinkles, by maintaining healthy skin, hair and nails.

The nutritional supplement herein described can be realized both in liquid or solid form, i.e. by mixing the ingredients in solid form or by lyophilizing the liquid preparation.

The nutritional supplement herein described comprises collagen in an amount between 0.5 and 10 g/50 ml, preferably in an amount between 1.75 and 7.5 g/50 ml, more preferably in an amount between 3 and 5 g/50 ml.

The collagen used in the liquid nutritional supplement can be hydrolyzed collagen, preferably deriving from a fish source.

Carnosine, preferably L-carnosine, is present in an amount between 10 and 250 mg/50 ml, preferably in an amount between 20 and 160 mg/50 ml, more preferably in an amount between 40 and 80 mg/50 ml.

The CoEnzyme Q10 is present in an amount between 5 and 250 mg/50 ml, preferably in an amount between 9 and 200 mg/50 ml, more preferably in an amount between 15 and 150 mg/50 ml.

The Resveratrol, preferably T-resveratrol, is present in an amount between 0.2 and 450 mg/50 ml, preferably in an amount between 1 and 200 mg/50 ml, more preferably in an amount between 2 and 80 mg/50 ml.

Collagen is the main component of skin together with elastin and hyaluronic acid and has a key role in providing integrity and elasticity.

However, collagen declines with age leading to a loss of the skin elasticity and to the formation of fine lines and wrinkles.

The hydrolysed collagen present in the nutritional supplement herein disclosed helps in stimulating fibroblast cells to produce new collagen (type I and III), hyaluronic acid and elastin (extracellular components in the dermis).

L-Carnosine is a protein building block that is naturally produced in the body. It is highly concentrated in muscles, brain, heart, and in many other parts of the body.

Coenzyme Q10 (CoQ10) is a vitamin-like substance found throughout the body, but especially in the heart, liver, kidney, and pancreas.

T-Resveratrol is an antioxidant polyphenol found in the skin of red grapes and in other fruits as well as in the roots of Japanese knotweed (*Polygonum cuspidatum*).

Due to the synergistic effects exerted by its main ingredients, i.e. collagen, L-Carnosine, Coenzyme Q10 and T-Resveratrol, the nutritional supplement herein described is endowed with a high antioxidant capability and it is able to reduce the oxidative damage to the integumentary system.

In particular, by counteracting the formation of free radicals, it exerts an improvement in the skin condition by increasing its elasticity and firmness, by decreasing dryness, depth and total surface of wrinkles. It also maintains healthy skin, hair and nails.

In another embodiment, the nutritional supplement further comprises an emulsion comprising borage seed oil and primrose oil.

The emulsion comprising borage seed oil and primrose oil can be present in an amount between 0.5 and 250 mg/50 ml, preferably in an amount between 2 and 200 mg/50 ml, more preferably in an amount between 5 and 150 mg/50 ml.

By adding the emulsion comprising borage seed oil and primrose oil the supplement herein described surprisingly shows a potentiating effect on skin smoothness and hydration.

In particular, the emulsion comprising borage seed oil and primrose oil contains gamma-linolenic acid (GLA), also named omega-6 fatty acid, which is able to improve skin smoothness and hydration.

In another embodiment, the nutritional supplement comprises at least one further ingredient selected among hyaluronic acid, lycopene and black pepper extract.

The hyaluronic acid can be present in an amount between 0.5 and 100 mg/50 ml, preferably in an amount between 1 and 75 mg/50 ml, more preferably in an amount between 2 and 40 mg/50 ml.

The lycopene can be present in an amount between 0.01 and 40 mg/50 ml, preferably in an amount between 0.05 and 10 mg/50 ml, more preferably in an amount between 0.1 and 5 mg/50 ml.

The black pepper extract, known to enhance bioavailability of several substances by increasing their gastrointestinal absorption, can be present in an amount between 0.2 and 3.5 mg/50 ml, preferably between 0.5 and 2.5 mg/50 ml, more preferably in an amount between 1 and 2 mg/50 ml.

Hyaluronic acid (HA) is a high molecular weight polysaccharide (10-104 KDa), localized in the extracellular matrix of connective tissues, mainly in soft connective tissues, in particular skin. HA is formed by alternating units of Glucoronic acid and N-acetylglucosamine.

Lycopene belongs to the family of carotenoids and is present in many fruits and vegetables.

The present Inventors found that by adding at least one of hyaluronic acid, lycopene and black pepper extract to the nutritional supplement a further potentiating effect was obtained in terms of skin hydration, antioxidant activity and bioavailability of several substances.

In a further embodiment of the present disclosure, the nutritional supplement also includes at least one ingredient selected among acai berry, pomegranate, vitamin, preferably vitamin C and vitamin A.

Other vitamins that may be present in the nutritional supplement are any vitamins known to have a health benefit to consumers.

Preferably, further vitamins are selected from the group consisting of vitamin $B_1$, vitamin $B_2$, vitamin $B_3$, vitamin $B_6$, vitamin $B_{12}$, vitamin D, biotin and other water soluble vitamins.

In a further embodiment of the present disclosure the nutritional supplement herein described also includes minerals, additives and flavouring substances.

The minerals may be chosen between Zinc and Copper.

The additive is preferably selected among citric acid anhydrous, phosphoric acid, lactic acid, tartaric acid, DL-malic acid and sucralose.

Flavouring substances may be selected among peach and lychee essential oils.

Lactones, esters, aliphatic higher alcohols, ketones, aromatic aldehydes, aromatic alcohols, thioethers, fatty acids, propylene glycol, ethanol, glycerol (glycerine) were used to formulate the flavor base.

Table 1 reports the content range of the ingredients that can be included in the water based nutritional supplement as described above.

TABLE 1

| Ingredients | Content range/50 ml |
|---|---|
| Collagen (hydrolysed fish collagen) | 0.5-10 g |
| L-carnosine | 10-250 mg |
| CoEnzyme Q10 | 5-250 mg |
| T-Resveratrol | 0.2-450 mg |
| Hyaluronic acid | 0.5-100 mg |
| Evening Primrose Oil and Borage oil emulsion (20%) | 0.5-250 mg |
| Lycopene | 0.01-40 mg |
| Black pepper extract | 0.2-3.5 mg |
| Acai Berry Extract | 0-250 mg |
| Pomegranate | 0-250 mg |
| Vitamin C | 0-400 mg |

TABLE 1-continued

| Ingredients | Content range/50 ml |
|---|---|
| Vitamin A | 0-400 mg |
| Other vitamins | 0-400 mg |
| Minerals | 0-2.5 mg |
| Flavouring substances | 0-200 mg |

In the following some non limiting examples of different embodiments of the nutritional supplement object of the instant description will be provided.

EXAMPLE 1

The nutritional supplement in liquid form comprising the ingredients reported in Table 2 below has been prepared—according to the manufacturing process diagram shown in FIG. 1—first by adding ingredients such as water, Hyaluronic acid, Hydrolysed fish collagen, L-Carnosine, N-acetylglucosamine, Citric acid anhydrous, DL-malic acid, Black pepper extract, Zinc, Copper, D-biotin, Stevia, Pyridoxine hydrochloride, Soybean polysaccharide, Vitamin D3, Pomegranate concentrated juice, Acai berry extract, Coenzyme Q10, Lycopene, dissolved at a temperature of 60±5° C. in the mixing tank (A). Vitamin C (L-ascorbic acid) was then added to the mixture after cooling down the temperature to less than 45° C. Water and T-Resveratrol were then added into the mixing tank (B) at a temperature of 60±5° C. In a following step, the ingredients present in the mixing tank (A) and (B) together with the flavouring substances were added to the main batch tank. Water, borage oil and primrose oil emulsion (20%), d-α-tocopherol and β-carotene emulsion were then added into the mixing tank (B) cooling down the temperature to 25±5° C. and then added to the main batch tank. After mixing all the ingredients, water was added in order to adjust the volume to 50 ml. A quality control check was carried out to ensure the correct pH, acidity, taste and colour. In the final steps of the manufacturing procedure, the product went through steps of filtration and pasteurization at 98±2° C., held for 30 seconds before cooling down to 85±2° C. for the bottling process. A second step of pasteurization was done at 80±2° C., held for 30 seconds before final packaging.

TABLE 2

| Ingredients | Content 50 ml |
|---|---|
| Collagen (hydrolysed fish collagen) | 5.00 g |
| L-Carnosine | 60.0 mg |
| CoEnzyme Q10 | 25.0 mg |
| T-Resveratrol | 2.5 mg |
| Hyaluronic Acid | 40.0 mg |
| Evening Primrose Oil (*Oenothera biennis*), Borage Seed Oil (*Borago Officinalis*) (Solvent: Glycerol, Emulsifier: Soy Lecithin) | 25.0 mg |
| Lycopene | 0.10 mg |
| Black Pepper extract (Bioperine ®) | 1.50 mg |
| Acai Berry Extract | 30.0 mg |
| Pomegranate | 20.0 mg |
| Vitamin C (Ascorbic Acid) | 80.0 mg (100% NRV*) |
| Vitamin A (Betacarotene) | 150 μg (15% NRV*) |
| Vitamin D (D3) | 5 μg (100% NRV*) |
| Vitamin E (D-α-Tocopherol) | 6.0 mg (50% NRV*) |
| Vitamin B6 (Pyridoxine hydrochloride) | 1.65 mg (118% NRV*) |
| Copper | 0.15 mg (15% NRV*) |
| Biotin (D-Biotin) | 50 μg (100% NRV*) |
| Zinc (gluconate) | 1.50 mg (15% NRV*) |

TABLE 2-continued

| Ingredients | Content 50 ml |
|---|---|
| N-Acetylglucosamine | 5.0 mg |
| Citric Acid | 450.0 mg |
| Soybean polysaccharide | 200.0 mg |
| Malic Acid | 100.0 mg |
| Stevia | 30.0 mg |
| Flavouring | 0.2250 mg |
| Water | 43.873 g |

*NRV = Nutrient Reference Value

Table 3 below shows the nutritional information of the supplement herein disclosed.

TABLE 3

| Nutritional Information | Content 50 ml |
|---|---|
| Energy | 34 kcal (144 kJ) |
| Protein | 5.3 g |
| Carbohydrates (of which sugars) | 0.0 g (0.0 g) |
| Fat (of which saturates) | 1.4 g (0.4 g) |
| Fibre | 0.0 g |
| Sodium | 0.0 mg |

The nutritional supplement being substantially free of carbohydrates can be advantageously assumed also by people affected by diabetes.

EXAMPLE 2

The nutritional supplement in liquid form comprising the ingredients reported in Table 4 below has been prepared—according to the manufacturing process diagram shown in FIG. 1—first by adding ingredients such as water, Hyaluronic acid, hydrolysed fish collagen, L-Carnosine, N-acetylglucosamine, Citric acid anhydrous, DL-malic acid, Black pepper extract, Zinc, Copper, D-biotin, Stevia, Pyridoxine hydrochloride, Soybean polysaccharide, Vitamin D3, Pomegranate concentrated juice, Acai berry extract, Coenzyme Q10, Lycopene, dissolved at a temperature of 60±5° C. in the mixing tank (A). Vitamin C (L-ascorbic acid) was then added to the mixture after cooling down the temperature to less than 45° C. Water and T-Resveratrol were then added into the mixing tank (B) at a temperature of 60±5° C. In a following step, the ingredients present in the mixing tank (A) and (B) together with the flavouring substances were added to the main batch tank. Water, borage oil and primrose oil emulsion (20%), d-α-tocopherol and β-carotene emulsion were then added into the mixing tank (B) cooling down the temperature to 25±5° C. and then added to the main batch tank. After mixing all the ingredients, water was added in order to adjust the volume to 30 ml. A quality control check was carried out to ensure the correct pH, acidity, taste and colour. In the final steps of the manufacturing procedure, the product went through steps of filtration and pasteurization at 98±2° C., held for 30 seconds before cooling down to 85±2° C. for the bottling process. A second step of pasteurization was done at 80±2° C., held for 30 seconds before final packaging.

TABLE 4

| Ingredients | Content 30 ml |
|---|---|
| Collagen (hydrolysed fish collagen) | 5.0 g |
| L-Carnosine | 60.0 mg |

TABLE 4-continued

| Ingredients | Content 30 ml |
|---|---|
| CoEnzyme Q10 | 25.0 mg |
| T-Resveratrol | 2.5 mg |
| Hyaluronic Acid | 40.0 mg |
| Evening Primrose Oil (*Oenothera biennis*), Borage Seed Oil (*Borago Officinalis*) (Solvent: Glycerol, Emulsifier: Soy Lecithin) | 25.0 mg |
| Lycopene | 0.10 mg |
| Black Pepper extract (Bioperine ®) | 1.50 mg |
| Acai Berry Extract | 30.0 mg |
| Pomegranate | 20.0 mg |
| Vitamin C (Ascorbic Acid) | 80.0 mg (100% NRV*) |
| Vitamin A (Betacarotene) | 150 µg (15% NRV*) |
| Vitamin D (D3) | 5 µg (100% NRV*) |
| Vitamin E (D-α-Tocopherol) | 6.0 mg (50% NRV*) |
| Vitamin B6 (Pyridoxine hydrochloride) | 1.65 mg (118% NRV*) |
| Copper | 0.15 mg (15% NRV*) |
| Biotin (D-Biotin) | 50 µg (100% NRV*) |
| Zinc (gluconate) | 1.50 mg (15% NRV*) |
| N-Acetylglucosamine | 5.0 mg |
| Citric Acid | 450.0 mg |
| Soybean polysaccharide | 200.0 mg |
| Malic Acid | 100.0 mg |
| Stevia | 30.0 mg |
| Flavouring | 0.2253 mg |
| Water | 23.873 g |

*NRV = Nutrient Reference Value

The liquid nutritional supplements realized as described above administered to humans reduced the oxidative damage to the integumentary system.

In particular, by counteracting the formation of free radicals, the liquid nutritional supplement intake reduced skin dryness, improved skin firmness and elasticity, and exerted an anti-aging effect by decreasing depth and total surface of wrinkles.

It also acted on the follicle function reducing hair loss and maintaining healthy nails.

The realization of the nutritional supplement is not limited to these examples but can have variants, which are not exceeding the limits of the underwritten claims.

In the following different combinations of the main ingredients contained in the nutritional supplement object of the instant disclosure were tested to investigate their synergistic effect on metalloproteinases activities.

Materials and Methods

Cell Culture

Adult normal human dermal fibroblasts NHDF-ad (Lonza) were grown in fibroblast growth media (FGM) (Lonza) with 2% foetal bovine serum (FBS). 24 well culture plates were seeded at a density of 50,000 cells/well and incubated at 37° C. and 5% $CO_2$. The cells were allowed to attach for 24 hours before 250 µl fresh media was added to each well (FGM with 0.3% FBS, 100 µM ascorbic acid and 100 µg/ml 500 kDa dextran sulphate, to induce serum starvation and macromolecular crowding) with the test ingredients, in duplicate, for 48 hours.

The positive control considered for this study was 5 ng/ml recombinant human TGFβ1 (Peprotech) in crowded media and the negative control was crowded media alone.

The ingredients tested are listed in Table 5.

TABLE 5

| Constituent | Abbreviation | Concentration (μg/ml) |
| --- | --- | --- |
| Hydrolysed piscine collagen | C | 2000 |
| Carnosine | CS | 24 |
| CoEnzyme Q10 | Q10 | 10 |
| Resveratrol | R | 1 |

The various combinations of the ingredients tested is provided in Table 6.

TABLE 6

| Number | Combination |
| --- | --- |
| 0 | Media alone |
| 1 | C |
| 2 | C + CS |
| 3 | C + CS + Q10 |
| 4 | C + CS + Q10 + R |

After 48 hours of incubation with the various ingredients combinations, the supernatants (cleared of cells) were harvested for evaluation of metalloproteinase MMP-1, MMP-3 expression.

Sample Preparation

Cells were lifted from the wells by adding 168.75 μl HBSS —Ca/Mg and 18.75 μl (10×) trypsin-EDTA (Sigma) to each well, incubated at 37° C. for 20 minutes with shaking, and then samples removed into tubes containing 62.5 μl, 1 M oxalic acid, ensuring the sample is mixed. The samples in acid were heated for 1 hour at 95-100° C.

ELISA Measurements

Total MMP-1 and total MMP-3 were measured using methods as described by the relevant established ELISA kit (R&D Systems).

Results

The effect of the addition of the ingredients of the nutritional supplement herein disclosed on MMP-1 and MMP-3 synthesis by NHDF cells was evaluated.

NHDF cells were treated for 48 hours in either media alone (0), or with the addition of various main ingredients combinations (1-4, see Tables 5 and 6 in Materials and Methods section for details).

The ingredients, as described in Tables 5 and 6, were tested and compared to the effect of media alone (0; 100%).

MMP-1, MMP-3 Synthesis

MMP-1 and MMP-3 synthesis were measured in the supernatant alone where they were most abundant.

MMP-1

Figure 3:
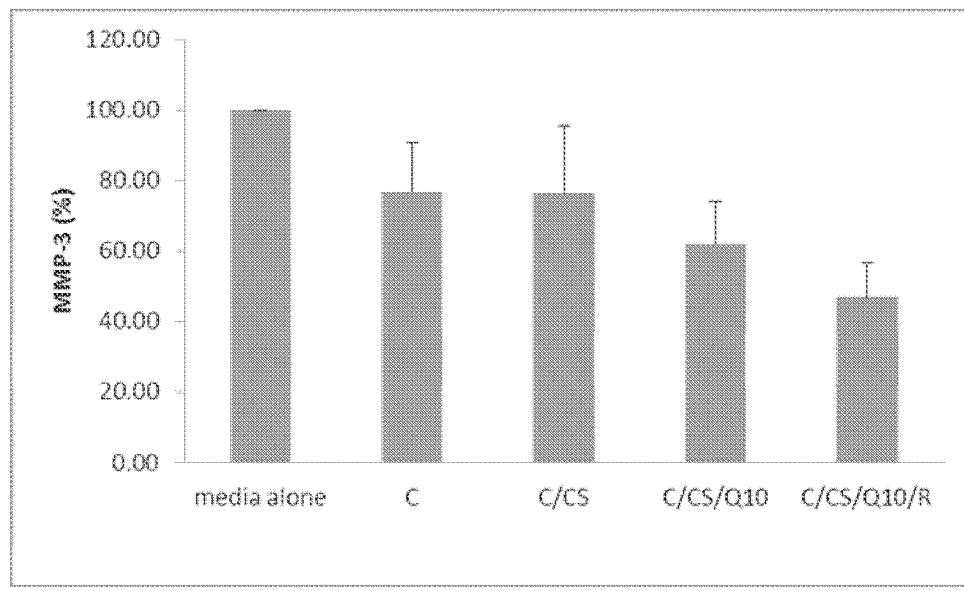
FIG. 3 shows the effect of nutritional supplement main ingredients on MMP-3 synthesis by normal human dermal fibroblasts (NHDF). MMP-3 was measured in supernatants of NHDF grown in 24 well plates and incubated in media (0) plus various combinations of nutritional supplement main ingredients (see tables 5 and 6 for description of additions) for 48 hours. Data was expressed as % of media control, normalised to 100% in each experiment and is presented as mean±SEM of 3 independent experiments.*indicates $P<0.05$, $P<0.01$,* $P<0.001$,**** $P<0.0001$. Media control is $0.6\pm0.3$ ng/ml.

A highly significant decrease in supernatant MMP-1 protein levels (FIG. 3) was seen in response to addition of other main constituents of the nutritional supplement object of the instant description (1; 65.3±13.2%, 2; 83.3±13.2%, 3; 64.6±12.5%, 4; 47.2±9% of media control).

MMP-3

Similarly, MMP-3 was significantly decreased in supernatants in response to addition of other main constituents of the nutritional supplement object of the instant description (FIG. 4) (1; 76.9±13.7%, 2; 76.4±19%, 3; 62.1±12%, 4; 47±9.6% of media control).

The results witnessed herein demonstrate the anti-ageing, antioxidant efficacy of the nutritional supplement herein disclosed in the improvement of the integumentary system.

The ingredients were tested on normal human dermal fibroblasts.

The expression of cell MMPs was evaluated to check if their levels were reduced due the anti-oxidant activity of the ingredients tested.

The results have shown a significant decrease in MMP-1 and MMP-3 synthesis in the supernatant with the nutritional supplement object of the instant description.

These data suggest a benefit of the nutritional supplement in restoring the homeostasis of the extracellular matrix.

The effect observed on metalloproteinases suggests that the antioxidant properties of the nutritional supplement reduce the collagen/elastin degradation in the skin.

Naturally, while the principle of the invention remains the same, the details of construction and the embodiments may widely vary with respect to what has been described and illustrated purely by way of example, without departing from the scope of the present invention.

REFERENCES

Finkel, T. and N. J. Holbrook (2000). "Oxidants, oxidative stress and the biology of ageing." Nature 408(6809): 239-247.

Ganceviciene, R., A. I. Liakou, A. Theodoridis, E. Makrantonaki and C. C. Zouboulis (2012). "Skin anti-aging strategies." Dermatoendocrinol 4(3): 308-319.

Guo, H., Huang, K., Zhang, X., Zhang, W., Guan, L., Kuang, D., Deng, Q., Deng, H., Zhang, X., He, M., Christiani, D., Wu, T. (2014). "Women are more susceptible than men to oxidative stress and chromosome damage caused by polycyclic aromatic hydrocarbons exposure". Environ Mol Mutagen. [Epub ahead of print]

Hao, L., Huang, H., Gao, J., Marshall, C., Chen, Y., Xiao, M. (2014). "The influence of gender, age and treatment time on brain oxidative stress and memory impairment induced by d-galactose in mice". Neurosci Lett 571C:45-49.

Kohen, R. (1999). "Skin antioxidants: their role in aging and in oxidative stress—new approaches for their evaluation." Biomed Pharmacother 53(4): 181-192.

Kozina, L. S., I. V. Borzova, V. A. Arutiunov and G. A. Ryzhak (2012). "The role of oxidative stress in skin aging." Adv Gerontol 25(2): 217-222.

Kunwar, A. and K. I. Pridashini (2011). "Free radicals, oxidative stress and importance of antioxidants on human health." J Med Applied Sci 1(2):3-60.

Levine, R. L. and E. R. Stadtman (2001). "Oxidative modification of proteins during aging." Exp Gerontol 36(9): 1495-1502.

Sohal, R. A. and R. Weindruch (1996). "Oxidative stress, caloric restriction, and aging". Science 273(5271): 59-63.

Turrens, J. F. and J. M. McCord (1990). "Free Radicals, Lipoproteins, and Membrane Lipids". Paulet, A. C.; Douste-Blazy, L.; Paoletti, R., editors. Plenum; New York: 203-212.

The invention claimed is:

1. A nutritional supplement for reducing oxidative damage to a subject's integumentary system consisting essentially of collagen, carnosine, CoEnzyme Q10, and Resveratrol,
   wherein collagen is present in an amount between 0.5 and 10 g/50 ml,
   carnosine is present in an amount between 10 and 250 mg/50 ml, CoEnzyme Q10 is present in an amount between 5 and 250 mg/50 ml, and Resveratrol is present in an amount between 0.2 and 450 mg/50 ml.

2. The nutritional supplement of claim 1, further comprising an emulsion comprising borage seed oil and primrose oil, hyaluronic acid, lycopene, black pepper extract, acai berry, pomegranate, and at least one vitamin selected from the group consisting of vitamin C, vitamin A, vitamin D, vitamin E, vitamin B1, vitamin B6, vitamin B2, vitamin B12, vitamin D, and biotin, wherein borage seed oil and primrose oil are present in an amount between 0.5 and 250 mg/50 ml, hyaluronic acid is present in an amount between 0.5 and 100 mg/50 ml, lycopene is present in an amount between 0.01 and 40 mg/50 ml, black pepper extract is present in an amount between 0.2 and 3.5 mg/50 ml, acai berry and pomegranate are present in an amount up to and including 250 mg/50 ml, and vitamin C, vitamin A, vitamin D, vitamin E, and/or biotin are present in an amount between up to and including 400 mg/50 ml.

3. A method to reduce oxidative damage to a subject's integumentary system, wherein the method comprises administering the nutritional supplement of claim 1 to the subject, and wherein the nutritional supplement reduces oxidative damage to the subject's integumentary system.

* * * * *